United States Patent [19]
Vago

[11] Patent Number: 4,942,868
[45] Date of Patent: Jul. 24, 1990

[54] ULTRASONIC TREATMENT OF ANIMALS

[75] Inventor: Robert E. Vago, Northbrook, Ill.

[73] Assignee: Malmros Holding, Inc., Morton Grove, Ill.

[21] Appl. No.: 175,936

[22] Filed: Mar. 30, 1988

[51] Int. Cl.⁵ ............................................. A61M 25/00
[52] U.S. Cl. .................................................... 128/24 A
[58] Field of Search ................ 128/24 A, 328, 660.03; 604/22

[56] References Cited

U.S. PATENT DOCUMENTS

| | | | |
|---|---|---|---|
| 2,970,073 | 1/1961 | Prange | 128/24 A |
| 3,499,436 | 3/1970 | Balamuth | 128/24 A |
| 3,499,437 | 3/1970 | Balamuth | 128/24 A |
| 3,867,929 | 2/1975 | Joyner et al. | 128/24 A X |
| 4,282,880 | 8/1981 | Gardineer et al. | 128/915 X |
| 4,501,151 | 2/1985 | Christman | 128/660.01 X |
| 4,614,178 | 9/1986 | Harlt et al. | 128/24 A |
| 4,698,058 | 10/1987 | Greenfeld et al. | 128/24 A X |

*Primary Examiner*—Francis Jaworski
*Attorney, Agent, or Firm*—Vincent L. Carney

[57] ABSTRACT

To provide ultrasonic treatment of animals, ultrasonic waves in a frequency range of between 15 kilohertz and 100 kilohertz are applied to water in a tub with a power density between 0.1 and 5 watts per square centimeter. The equipment is able to apply ultrasonic waves with at least two power densities in the vicinity of the portion of the animal with one of said power densities being more than 15 watts per square meter for sterilizing the water before the patient enters the tub and the other being less than 15 watts per square meter.

22 Claims, 5 Drawing Sheets

ULTRASONIC TREATMENT OF ANIMALS

BACKGROUND OF THE INVENTION

This invention relates to methods and equipment for treating animals including humans with ultrasonic waves for purposes of hygiene and therapy such as for example cleaning, microbicidal and antifungal activity and the promotion of epithelial healing.

In one class of ultrasonic treatment, ultrasonic sound is applied to a working fluid by a transducer. The part of the animal to be treated is immersed in the working fluid and the transducer transfers vibrations in the ultrasonic range to that animal through the working fluid.

In one prior art type of ultrasonic treatment of this class, ultrasonic sound is applied to patients in a range of power levels of from 0 to 5 watts per square centimeter at frequencies in the megahertz range extending from approximately ¼ megahertz to 3 megahertz. Vibrations of this general type have been used for therapy to human beings in the prior art. It is generally used for stiff joints and muscular disorders.

This therapeutic treatment has several deficiencies, such as for example: (1) it increases the risk of overheating the underlying tissue of patients; (2) it is not useable for hygienic purposes; and (3) it has not been known to have antiviral, antibacterial or antifungal activity, has not been used intentionally to accomplish this purpose, and thus has not be applied in a manner to accomplish antiviral, antibacterial or antifungal activity in an effective manner.

It is known to clean industrial articles with ultrasonic waves transmitted through a liquid medium. In this cleaning technique, the cleaning bath container is constructed of stainless steel and an ultrasound generator is epoxy-bonded to the bottom surface. Cavitation is introduced by large power vibrations well over 100 adjusted decibels in a frequency range which is typically between 20 to 60 kilohertz. The applied power is in a range from a few hundred watts to several kilowatts depending on the cleaning application.

This type of ultrasonic treatment device has a disadvantage in that it might be harmful to human beings. For example, the cavitation in the liquid may be induced through human tissue and cause cavitation in the blood stream or damage to tissue.

SUMMARY OF THE INVENTION

Accordingly, it is an object of the invention to provide a novel apparatus for ultrasonic treatment of animals.

It is a further object of the invention to provide a novel method for ultrasonic treatment of animals.

It is a still further object of the invention to provide a novel technique for treating animals with ultrasonic waves which provide hygienic and therapeutic benefits without being irritating or harmful to the animals.

It is a still further object of this invention to utilize ultrasonic waves efficiently in a frequency range which is beneficial to animals.

In accordance with the above and further objects of the invention, apparatus for ultrasonic treatment includes a container holding a working liquid and means for generating vibrations in the working liquid in a frequency range and in a power range that are not irritating or harmful to animals, including humans, and yet which produce one or more beneficial effects, such as for example, cleaning or antimicrobial or therapeutic effects.

The container in the preferred embodiment is a bathtub but may be smaller such as for example a small container sufficient to immerse a part of the human body such as a foot. The frequency range and power are selected together to avoid transient cavitation in the bather but yet produce sufficient oscillation for cleaning or to destroy certain microbes such as harmful bacteria or fungus on the skin and in the liquid within the container.

The frequency that is used is in the range of frequencies between 15 and 100 kilohertz and the power density is less than 15 watts per square centimeter, although the cleaning efficiency begins to drop as the frequencies exceed 80 kilohertz and some detectable feeling is obtained from power density over 5 watts per square centimeter. The preferred frequency is substantially 26.5 kilohertz and the preferred power density for bather exposure is 0.1 to 5.0 watts per square centimeter although variations may be made in the two to provide the desirable beneficial effect while avoiding harm to the bather.

To sterilize the water before bathing, the power density of the ultrasound is increased to a level sufficient to destroy microbes. The ultrasound is applied at a frequency selected for efficiency in destroying the microbes with the lowest power consistent with sterilization and with acceptable radiation levels of sound to the air. This power density is above 15 watts per square centimeter and at a frequency above 15 kilohertz but may be selected for the circumstances. Additives, such as detergents or antiseptics may be added. This procedure may also be used to sterilize inanimate objects in the liquid.

Generally in manufacturing a bath, the size of the container, the liquid, the frequencies of sound, and the power of transmission are selected to provide the cleaning, therapeutic or microbicidal benefits while avoiding deleterious effects. Although these factors are al 1 considered during product design and use, the order of selection is generally: (1) the size of the container in connection with the purpose such as for a foot bath or for full bathing of a human or the like; (2) the nature of the liquid, such as degassed water, water with a mild detergent or with a mild antiseptic; (3) the frequency or the sequence of different frequencies to be applied in connection with the purpose; and (4) the power or sequence of powers effective for the desired purpose. After a theoretical selection, the values are adjusted to avoid any observed undesirable effects such as standing waves or irritating sound transmission.

The liquid is generally water and preferably degassed water with a mild detergent. The housing of the sound generator and the bath container wall are designed to absorb sound and thus reduce acoustical radiation or other undesired effects. Precautions are taken to avoid risk of electric shock of a bather.

To use the ultrasonic treatment in accordance with the invention, water is degassed, a tub is filled with degassed water and a mild detergent is added. The patient is immersed in the water, or if desired, a single part of the body such as the foot is immersed in the water and ultrasonic sound is transmitted through the water. The sound is transmitted by applying oscillations to a magnetostrictive transducer which communicates with the water through a stainless steel plate in the side of the tub to create vibrations at a selected frequency within a frequency range of 15 through 100 kilohertz and preferably at 26.5 kilohertz with a power density of less than 15 watts per square centimeter and preferably 0.1 to 5.0 watts per square centimeter.

For safety, a meter measures the power density so observers can determine if it is safe and automatic threshold devices reduce or shut power off should it become too large. Moveover, in some embodiments, a sensor detects a foreign object in the liquid during sterilization and shuts off or reduces the power to prevent harm to the object.

From the above description, it can be understood that the apparatus and method of this invention has several advantages over the prior art, such as: (1) it has hygienic, therapeutic and antimicrobial benefits while being harmless to animals; (2) it makes economical use of vibrating transducers by using attenuation water as a working fluid; and (3) it performs both cleaning and woundhealing while at the same time providing antiviral, antibacterial and antifungal activity in a manner making it suitable for treatment of certain particularly severe maladies such as severe burns.

DESCRIPTION OF THE DRAWINGS

The above noted and other features of the invention will be better understood from the following detailed description when considered with reference to the accompanying drawings, in which.

DETAILED DESCRIPTION

Figures 1, 2, 3:
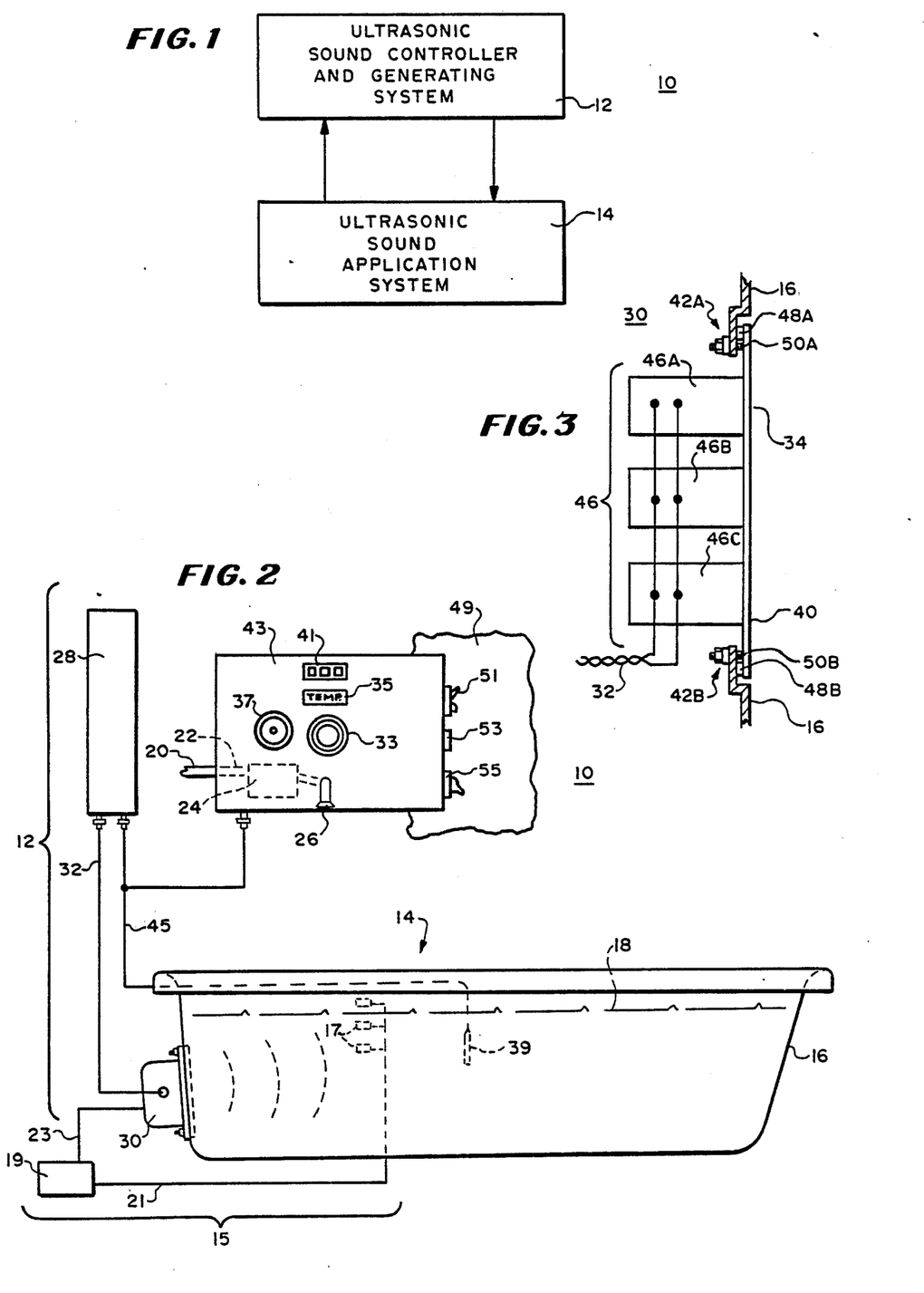
FIG. 1 is a block diagram of an ultrasonic treatment system in accordance with an embodiment of the invention.
FIG. 2 is a schematic diagram of a bathing system which is one form of the ultrasonic treatment system of FIG. 1.
FIG. 3 is a simplified schematic diagram of a transducer element positioned with respect to a container for working fluid in accordance with the invention.

In FIG. 1, there is shown a block diagram of an ultrasonic sound system 10 having an ultrasonic sound controller and generating system 12 and an ultrasonic sound application system 14 connected together to supply ultrasonic sound for hygienic, therapeutic and antimicrobial functions. The ultrasonic sound controller and generating system 12 is connected to and transmits signals to the ultrasonic sound application system 14, which may be a bathing system, to provide hygienic and therapeutic benefits to a bather.

In some embodiments, a transducer within the ultrasonic sound application system 14 supplies a feedback signal to the ultrasonic sound controller and generating system 12 for monitoring purposes. The ultrasound system 10 may aid in cleaning, may provide epithelial healing for an animal and particularly for humans and at the same time be actively bacteriocidal, viricidal and fungicidal.

The frequency of the vibrations is maintained in a range within 15 and 100 kilohertz and the power density is less than 15 watts per square centimeter, although the cleaning efficiency begins to drop as the frequencies exceed 80 kilohertz and some detectable feeling is obtained from power density over 5 watts per square centimeter. The preferred frequency is substantially 26.5 kilohertz and the preferred power density is 0.1 to 5.0 watts per square centimeter although variations may be made in the two to provide the desirable beneficial effect while avoiding harm to the bather.

To sterilize the water before bathing, the power density of the ultrasound is increased to a level sufficient to destroy microbes. The ultrasound is applied at a frequency selected for efficiency in destroying the microbes with the lowest power consistent with sterilization and with acceptable levels of sound radiation to the air. This power density is above 15 watts per square centimeters and at a frequency above 15 kilohertz but may be selected for the circumstances. Additives, such as detergents or antiseptics may be added. This procedure may also be used to sterilize inanimate objects in the liquid.

In FIG. 2, there is shown a schematic drawing of the ultrasonic sound system 10 showing one embodiment of ultrasonic sound controller and generating system 12 mounted to one type of ultrasonic sound application system 14. In this embodiment, the ultrasonic sound application system 14 includes a plastic bath tub 16 containing water as a working fluid 18 and a supply of water such as that available from the faucet 26 in a wall panel 49. In one embodiment, a control system 15 is connected to the bathing system to reduce or terminate high power density ultrasonic waves if a person intrudes into the body of water 18. The supply of water 20 is positioned for any preliminary processing necessary and for convenient transfer to the tub 16.

The tub 16 must be sufficiently strong to contain the body of water 18 and sufficiently large so that a human or other animal such as a pet may have the required portion of its body immersed in the body of water 18. In the preferred embodiment, the tub 16 is a bathtub but it may be a foot basin or pet bath or the like.

To supply degassed water, the supply of fluid includes a water pipe or the like 22 to receive water, a degasser 24 and a valve such as a faucet or the like 26 positioned so that water may flow through the water pipe 22 from a source such as a household source through the degasser 24 and into the tub 16 after degassing. There are many commercial degassers including those that work with a vacuum operating through a mesh or a membrane or the like and any such system is suitable.

The ultrasonic sound controller and generating system 12 includes an ultrasonic generator 28 for generating periodic electric signals and a transducer assembly 30 for converting the electric signals to vibrations that are transmitted through the body of water 18 for cleaning, epithelial therapy and microbicidal effects. The ultrasonic generator 28 receives power from the mains power source and may be adapted to utilize either 115 or 230 volt, 60 hertz input power or 50 hertz input power. It is electrically connected by cable to the transducer assembly 30 for supplying vibrations within a frequency range and power which is not irritating or harmful to the patient nor to persons nearby because of sound radiation from the transducer assembly or water to the air.

In the preferred embodiment, a frequency of 26.5 kilohertz is used. The power density for degassed water at this frequency is approximately 0.1 to 5.0 watts per square centimeter but for partially degassed air any absolute value is lower by 0.1 watts per square centimeter and for somewhat gassy air is lower by 0.2 watts per square centimeter. The specific frequency need not be 26.5 Khz (kilohertz) but is preferred in the range of 20 Khz plus or minus 15 Khz.

To control the comfort of the patient within the ultrasonic sound system 10, the temperature of the water from the faucet 26 is controlled by mixing different proportions of cold and warm water as set by the dial 33 and indicated in the temperature gauge 35. Similarly, the power density emitted by the transducer assembly 30 is adjustable by the dial 37 and the power of the vibrations in the bath as measured by a transducer 39 is shown on the LED display 41.

To apply signals of the selected frequency and intensity to the ultrasound transducer assembly 30, the ultrasonic generator 28 is electrically connected to the ultrasound transducer assembly 30 by a cable 32 and both the ultrasonic generator 28 and control panel 43 are electrically connected to the transducer 39 to receive feedback signals through a cable 45. The control panel 43 also contains other normal electrical devices which are not part of the invention such as a ground fault interrupter 51, fuses 53 and a mains power switch 55.

Although in the embodiment of FIG. 2, the transducer 39 is positioned near the expected location of a bather, in the preferred embodiment, a transducer will be located in the assembly 30 on an inner plate described hereinafter and connected to the cable 45. The circuit will be calibrated at the factory using a transducer located at the expected location of a bather to obtain values corresponding to feedback signals from the transducer on the inner plate.

In some embodiments, a control system 15 includes a plurality of sensors 17 electrically connected to a detector 19 which in turn is connected to the ultrasonic generator 28 for control purposes. The sensors 17 are capacity sensors mounted to the tub 16 to detect an increase in the level of water due to the intrusion of a person into the water. Instead of capacity detectors which detect an increase in the level of the water, other types of detectors may be used including sonic detectors that detect a person near the surface of the water or heat detectors or the like. These detectors supply a signal to the ultrasonic generator 28 when the ultrasonic generator 28 is utilizing high power for sterilization purposes. It is intended to prevent a person from entering the tub while the high power is being applied to avoid harm.

For this purpose, the circuit 19 detects an increase in the level of water as a change in capacitance, differentiates the received signal and applies it to one input of an AND gate. The other input of the AND gate, if energized by the presence of high power signals, will de-energize the ultrasonic generator 28 so that the power is instantaneously eliminated. Instead of terminating the power, a resistance may be inserted in circuit with the electric signal from the ultrasonic generator 28 to reduce the power. These changes occur quickly before harm can be done to the patient.

In FIG. 3, there is shown a schematic diagram of the ultrasound transducer assembly 30 electrically connected by the cable 32 to the ultrasonic generator 28 (FIG. 2). The ultrasound transducer assembly 30 includes an interface and a transducer body connected together so that the transducer body generates mechanical vibrations in a selected frequency range and imparts them to the interface which in turn imparts them to the body of water 18.

To generate vibrations, the transducer body includes three transducer elements 46A, 46B and 46C electrically connected to the cable 32 and in series with each other to vibrate in synchronism and thus impart vibrations to the interface. The transducers in the preferred embodiment are magnetostrictive transducers but other types of transducers may be utilized such as piezoelectric transducers or the like. Moreover, an electrically actuated transducer may be positioned near the ultrasonic generator 28 (FIG. 2) and separated from the interface if desirable, with a long acoustic coupling such as a pneumatic coupling being utilized to transfer vibrations to the interface and ultimately to the body of water 18.

To transmit vibrations to the working fluid, the interface includes a vibrating plate 40 and a plurality of fasteners two of which are shown at 42A and 42B to mount the vibrating plate 40 to the plastic container or bath tub 16. In the preferred embodiment, one side of the vibrating plate 40 is mounted to a housing for the ultrasound transducer assembly 30 and the other side is positioned to be in contact with the body of water 18 in a manner to be described hereinafter.

The fastener means 42A and 42B include corresponding studs 50A and 50B welded to the vibrating plate 40 and adapted to have threaded upon them corresponding nuts which compress corresponding gaskets 48A and 48B against the edges of the tub 16, with the main portion of the vibrating plate 40 being on one side of the tub 16 and the transducers on another side so that the vibrating plate 40 is moved by the transducers with respect to the wall of the tub 16 and compresses and decompresses the gaskets 48A and 48B without permitting fluid to leak therethrough.

To further reduce lost energy and possible irritating or harmful effects, the tub 16 (FIG. 2) is designed to reduce sound transmission to the air and standing waves within the water. As part of this design, the wall of the tub 16 material is a sound absorbant plastic which is particularly absorbent to the frequency of the transducers.

Figure 4:
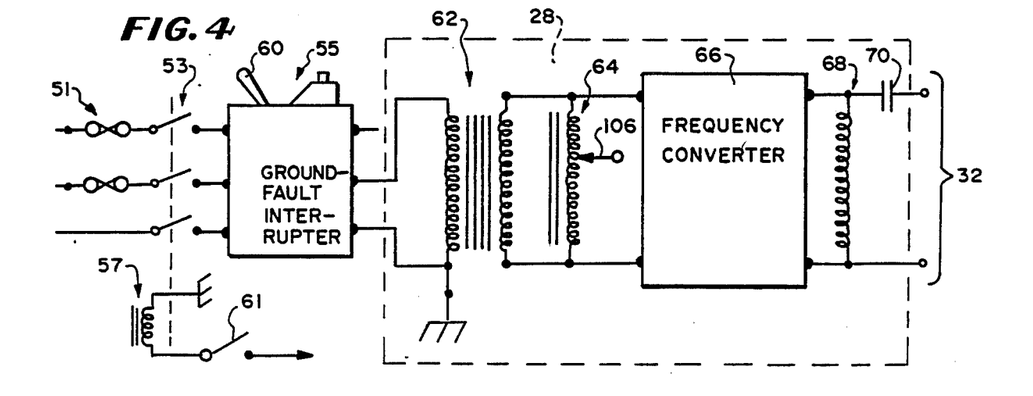
FIG. 4 is a schematic diagram of an ultrasonic generator useful in the embodiment of FIG. 3.

In FIG. 4, there is shown a schematic circuit diagram of a portion of the ultrasonic generator 28 connected to the ground fault interrupter 55 and fuses 51 through a mains power switch 53. The ground fault interrupter 55 may be of any suitable type containing a manual switch 60 and an internal switch triggered by current to ground of the order of 5 milliamperes to open the circuit. Suitable ground fault interrupters may be purchased from Arrow-Hart, under Model No. 9F2091MI. The mains power switch 53 may be manually controlled and is, in one embodiment, also controlled by a solenoid 57 to permit it to return to its normally open position when the power density in the ultrasonic sound application system 14 (FIG. 2) exceeds a preset limit in a manner to be described hereinafter.

The ultrasonic generator 28 includes an isolation transformer 62, an autotransformer 64, a frequency converter 66, an output matching inductor 68 and an output isolation capacitor 70. The isolation transformer 62 receives a 115 volts AC on its primary and conducts to the frequency converter 66 a reduced voltage under the control of the autotransformer 64 which may be adjusted to the potential applied to the frequency converter 66.

To generate 26.5 kilohertz cycles at a power under the control of the autotransformer 64, the frequency converter 66 may be of any suitable type, many of which are available on the market. In the preferred embodiment the frequency converter is a swept freqency generator having a carrier frequency of 26.5 Khz modulated at 100 to 120 hertz at a sweep rate of plus or minus 1 kilohertz. By sweeping the frequency across 2 kilohertz, the sound transmission to air is reduced by eliminating resonance problems. A suitable frequency converter is sold by Swen Sonic, Inc. The isolation transformer 62 includes taps to permit either 120 or 240 volt operation.

Figure 5:
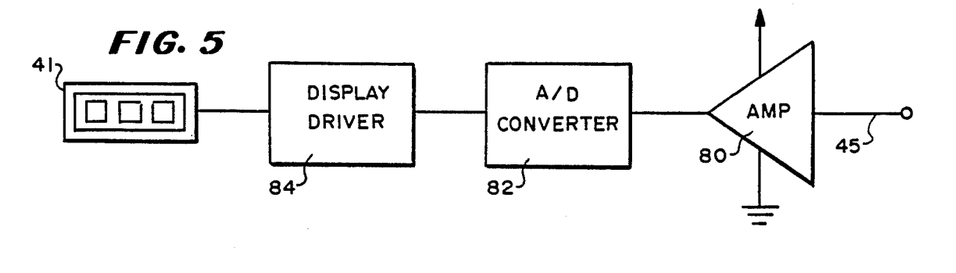
FIG. 5 is a block diagram of a power density display forming a part of the embodiment of FIGS. 1 and 2.

In FIG. 5, there is shown a block diagram of a circuit for receiving signals from the transducer 39 (FIG. 2) and providing a readout of the power density of the ultrasonic waves on the LED display 41. This circuit includes an amplifier 80, an analog-to-digital converter 82 and a display driver 84. These units by themselves are not part of the invention and are commercial units sold under the following designations: (e.g., Linear Technology Operational Amplifier LT1014DN). The operational amplifier is connected to cable 45 to receive signals representing the power density of the ultrasonic frequency, which it smooths and converts to a varying DC signal. Its output is electrically connected to the analog-to-digital converter 82 which converts the DC signal to a digital code for application to the display driver 84, which in turn drives the LED display 41 to indicate the power density in watts per square centimeter of the power of the ultrasonic sound in the body of water 18 (FIG. 2) received by the transducer 39 (FIG. 2). The amplifier 80 has a time constant which results in a DC output from the ultrasonic vibrations representing the total power impinging against the transducer 39 within the water 18 (FIG. 2).

Figure 6:
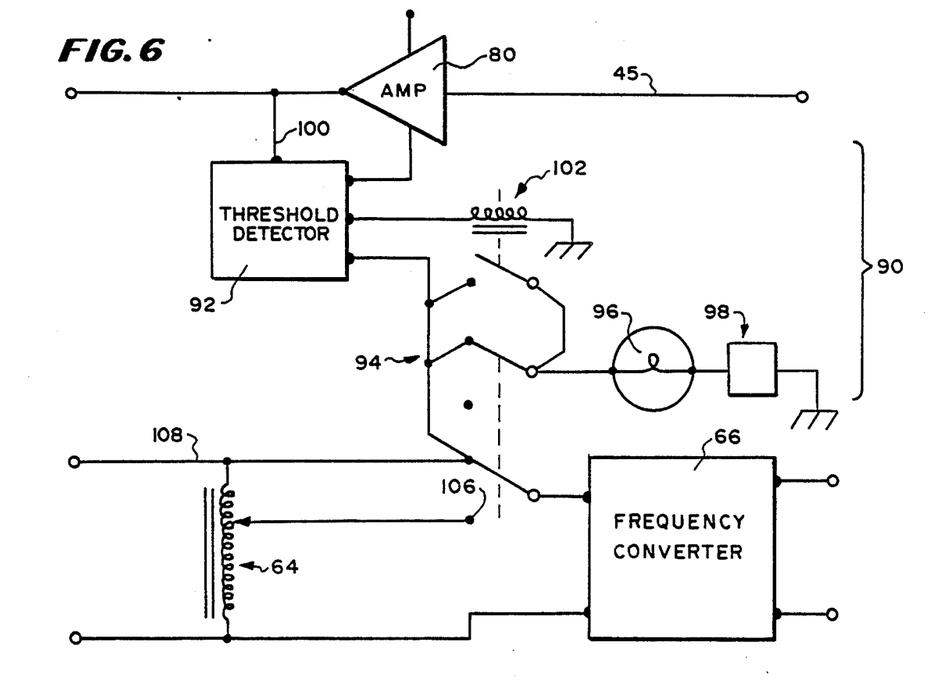
FIG. 6 is a schematic circuit diagram of an embodiment of feedback circuit useful in practicing the invention.

In FIG. 6, there is shown a feedback circuit 90 connected between the output of the amplifier 80 (FIG. 5) and the input to the frequency converter 66 (FIG. 4) to control the power of the ultrasonic vibrations. It includes a threshold detector 92, a three-pole double-throw, relay operated switch 94, a warning lamp 96 and a flasher 98.

To protect against too large a power density, the threshold detector 92 is connected to receive signals from the output of the amplifier 80 through conductor 100 and has a first output electrically connected to the solenoid 102 of the three-pole double-throw, relay operated switch 94. With this connection, the threshold detector 92 energizes the solenoid 102 to throw the three-pole double-throw, relay operated switch 94 from its normal position in which the frequency converter 66 (FIG. 6) receives the full output from the autotransformer 64 shown in FIG. 6 to its energized position in which the frequency converter receives the output from tap 106 of the autotransformer 64 upon the detector 39 (FIG. 2) reaching a power density greater than 5.0 watts per square centimeter at a modulation of 26.5 kilohertz, 100Az, at 80 to 90 percent amplitude and a sweep rate of plus or minus 1 kilohertz.

The three-pole double-throw, relay operated switch 94 may be manually set to make contact with tap 106 on the autotransformer 64 to provide a reduced power to the frequency converter 66 for cleaning action or, in the alternative, to its antimicrobial position where the frequency converter 66 is directly connected across the autotransformer 64 at conductor 108 to receive full power. If the power exceeds the predetermined limit in the threshold detector 92, the relay coil 102 is energized to reswitch the three-pole double-throw, relay operated switch 94 back to the autotransformer tap 106, thus reducing power. If the power is not reduced, the threshold detector 92 applies signal to the three-pole double-throw, relay operated switch 94 and the flasher 98 to permit a manual reset of the three-pole double-throw, relay operated switch 94.

Figure 7:
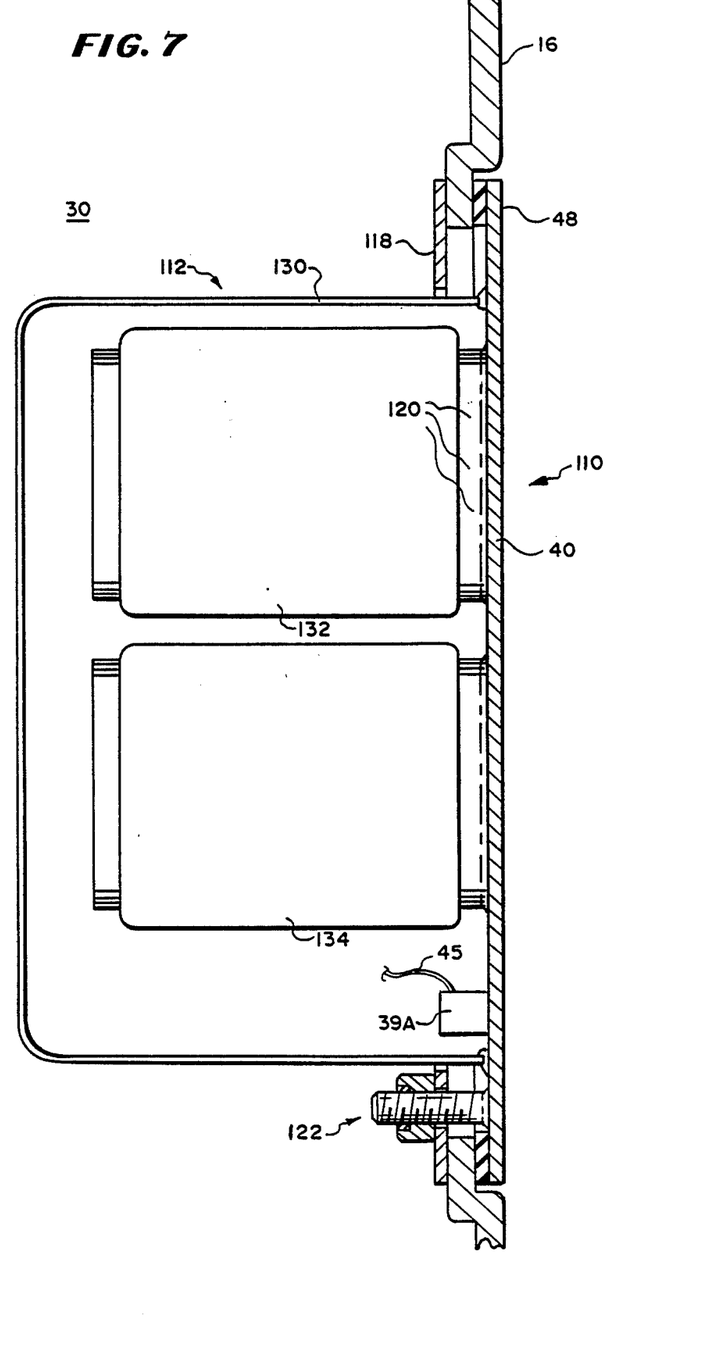
FIG. 7 is a sectional view of a transducer assembly forming part of FIGS. 1 and 2.

In FIG. 7, there is shown an elevational sectional view of the ultrasound transducer assembly 30 (FIG. 2) having a vibrating plate assembly 110 and a magnetostrictive vibrator assembly 112. The vibrating plate assembly 110 includes a stainless steel vibrating plate 40, and elastomeric seal 48, a clamping collar 118, a plurality of nickel laminations 120 and a plurality of antivibration fasteners, one of which is shown at 122. The plate itself may be circular or rectangular having a thickness of approximately $\frac{1}{8}$ inch and an area enclosed within substantially an 8-inch diameter in the preferred embodiment. However, its size is determined by the need to transmit sufficient power through the water for the desired purposes such as hygienic, antimicrobial or therapeutic.

The vibrating plate 40 should be larger than the opening in the tub wall if it directly contacts the body of water 18 (FIG. 2). Preferably it is sealed to the edge of a corresponding aperture in the tub 16, with the magnetostrictive vibrator being outside of the tub 16 and clamped to the stainless steel vibrating plate 40. To provide sealing on the inside of the tub 16 against escape of the body of water 18 (FIG. 2), the elastomeric seal 48 in the circular plate version is an annular gasket having an outer diameter of approximately 3 9/16 inches, an inner diameter of approximately $3\frac{1}{4}$ inches and a length of approximately 31/32 inch. It rests between a recessed circular shoulder of the tub 16 and the outer periphery of the vibrating plate 40, being pulled tightly against it to prevent leakage of fluid.

To hold the elastomeric seal 48 tightly between the vibrating plate 40 and the tub 16, an annular clamping collar 118 circumscribes the housing of the magnetostrictive vibrator assembly 112. The annular clamping collar 118 is of stainless steel and includes a plurality of circumferentially spaced-apart apertures each adapted to receive through it a corresponding one of a plurality of shanks of the fasteners 122 which circumscribe the annular clamping collar 118. In the preferred embodiment, the fasteners 122 are bolts having their heads welded to the vibrating plate 40 in a circle with their shanks extending upwardly and their threaded portions passing through the corresponding holes in the annular clamping collar 118 at locations inward of the annular gasket 48 and approximately centered at a radius of $3\frac{5}{8}$ inches from the center of the annulus.

On the upper end of the shanks of the bolts are conventional external threads which receive a plurality of corresponding nuts in a manner to be described hereinafter to compress the annular clamping collar 118 and the vibrating plate 40 together between the annular gasket 48 and the wall of the tub 16. When held in this manner, the surface of the vibrating plate 40 that is in contact with the body of water 18 (FIG. 2) is flush with the inner surface of the tub 16, being recessed within a shoulder.

To vibrate the vibrating plate 40, the magnetostrictive vibrator assembly 112 includes a housing 130, a plurality of solenoid windings, two of which are shown at 132 and 134, and electrical connections to the solenoids extending through the housing (not shown in FIG. 7). The housing 130 is welded to the annular clamping collar 118 so that when the annular clamping collar 118 is clamped through the fasteners 122 to the vibrating plate 40, the ultrasound transducer assembly 30 is fastened to the tub 16 with the vibrating plate 40 in contact with the body of water 18 (FIG. 2) and the magnetostrictive elements positioned to vibrate the plate and electrically connected through cable 32 to the ultrasonic generator 28 (FIG. 2).

To vibrate the vibrating plate 40, the surface of the vibrating plate 40 adjacent to the coils such as 132 and 134 has welded to it a plurality of the nickel laminations 120 spaced throughout the surface adjacent to the three solenoid windings (two of which are shown at 132 and 134) so that when the solenoid windings are energized by the operating frequency, which in the preferred embodiment is 26.5 kilohertz, the vibrating plate 40 is vibrated to transmit vibrations through the body of water 18 in a substantially uniform manner with a power density controllable by the power applied to the ultrasonic generator 28 (FIG. 2).

Figure 8:
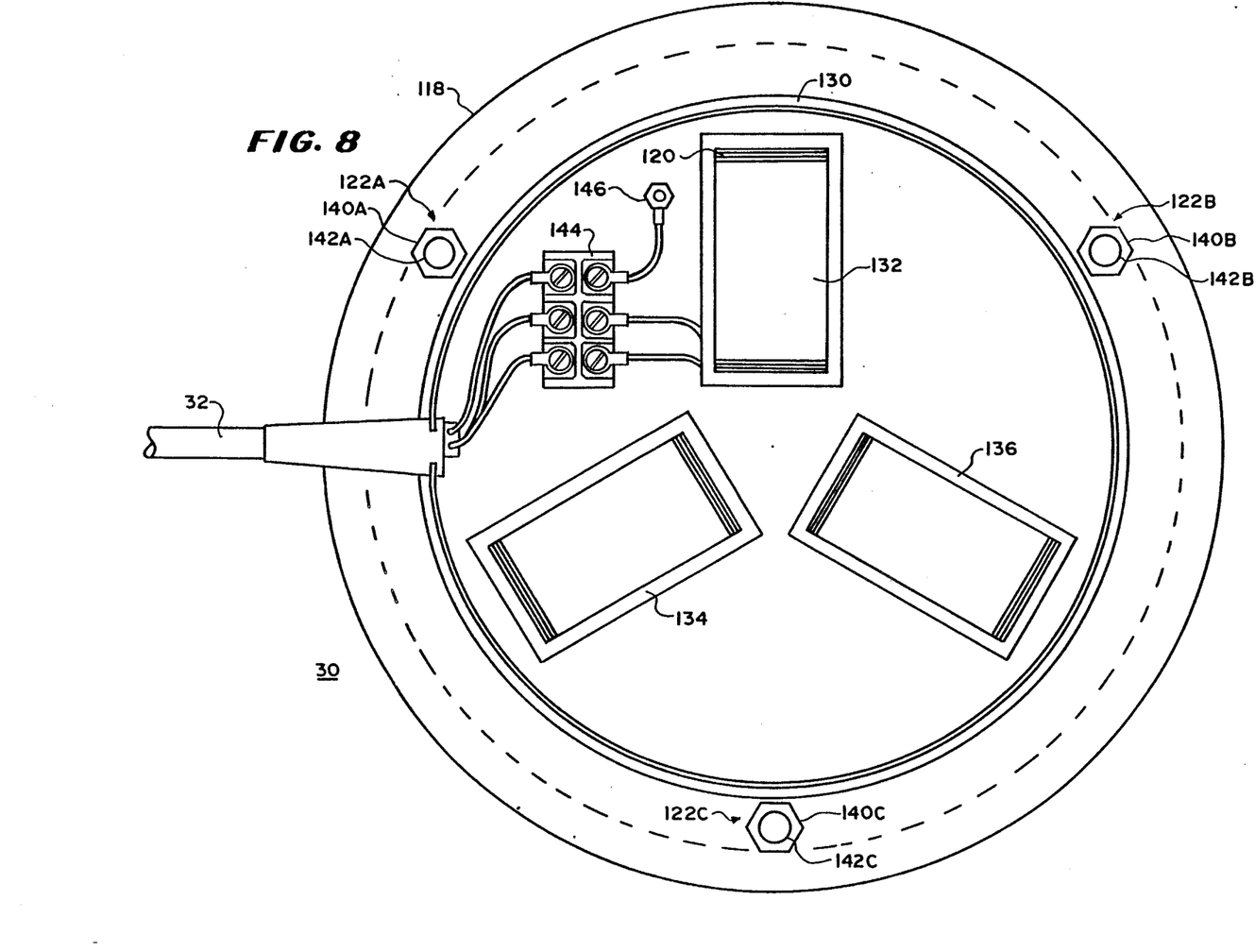
FIG. 8 is an elevational view of an internal portion of the transducer of FIG. 6.

In FIG. 8, there is shown a plan view of the circular version of the ultrasound transducer assembly 30 with the top of the housing 130 and the solenoid coils such as those shown at 132 and 134 (FIG. 7) removed. As shown in this view, there are three fasteners 122A-122C each containing a corresponding nut 140A-140C threaded onto a corresponding shank 142A-142C to hold the vibrating plate 40 (FIG. 7) to the annular clamping collar 118 and thus hold the housing 130 onto tub 16 (FIG. 2). The cable 32 enters the housing 130 and is connected to a terminal block 144, to provide a ground connection at 146 to the vibrating plate 40 (FIG. 7) and electrical connections to three solenoids, mounted above 132, 134 and 136 to activate the nickel laminations 120 on the vibrating plate 40. With this embodiment, the three series connected solenoids simultaneously pull the nickel laminations 120 inwardly and release them outwardly to impart vibrations to the body of water 18.

Figures 9, 10:
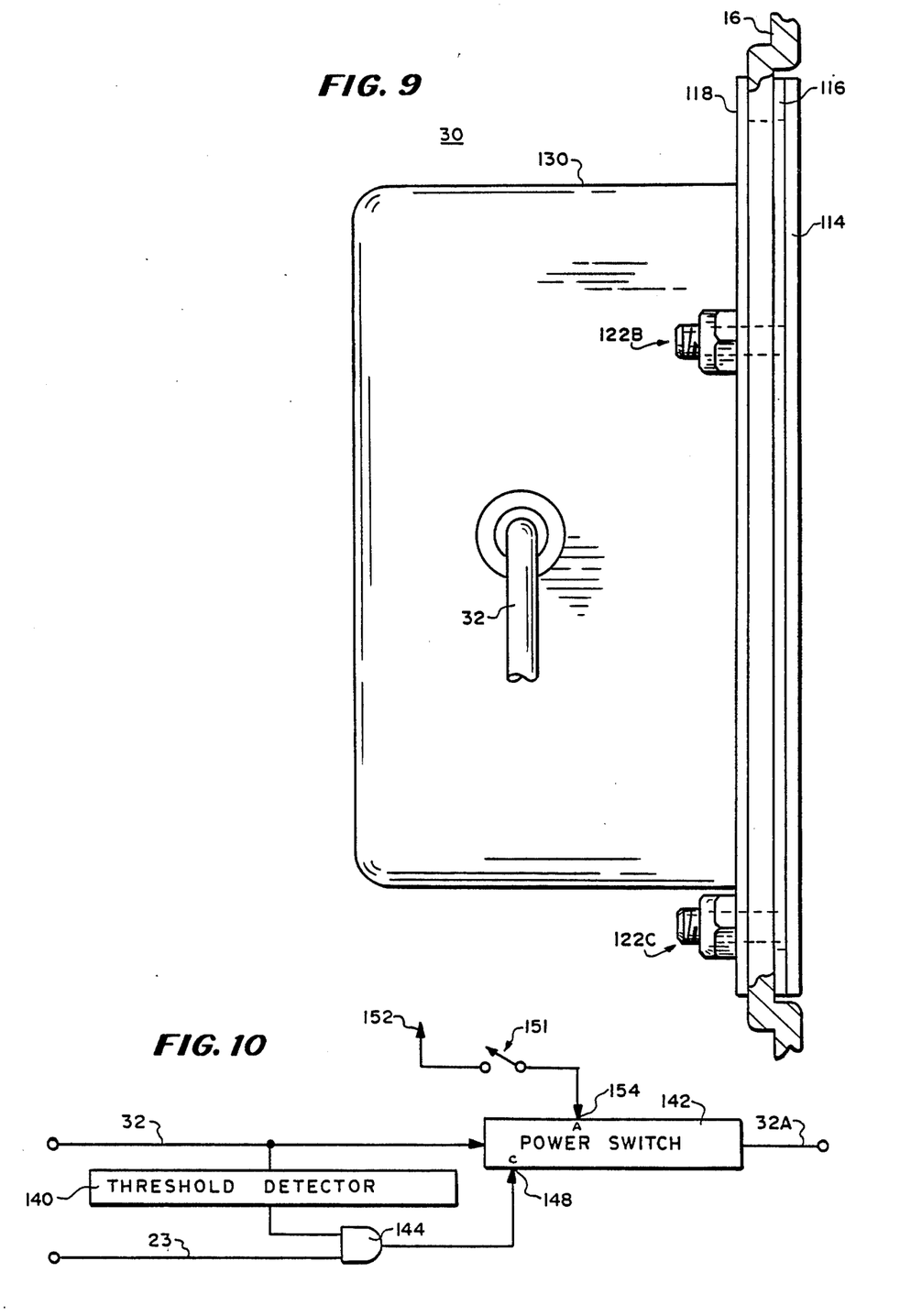
FIG. 9 is a side elevational view, partly broken away and sectioned, of the transducer element of FIG. 6.
FIG. 10 is a block diagram of a control system which may be part of the bathing system of FIG. 2.

In FIG. 9, there is shown a sectional view taken through the tub 16 to the side of the ultrasound transducer assembly 30 illustrating the manner in which the fasteners, two of which are shown at 122A and 122C. As shown in this view, the cable 32, which is a twisted and shielded conductor pair with a plastic covered sheath and elastomeric strain relief connection extends from the housing 130 to be connected to the ultrasonic generator 28 (FIG. 2). In an embodiment having the detector 39A (FIG. 7) bonded to the plate 40 (FIGS. 3 and 7), the cable 32 may contain the conductors 45 as well.

In FIG. 10 there is a block diagram of a circuit suitable for including in the control system 15 in circuit with cable 32 for the purpose of controlling the generation of ultrasonic waves including a threshold detector 140, a power switch 142 and an AND gate 144.

The power switch 142 has its input electrically connected to cable 32 to receive signals from the ultrasonic generator 28 (FIG. 2) and has its output electrically connected to the transducers 132, 134 and 136 (FIGS. 7 and 8) to apply oscillations to the transducers and thus transmit ultrasonic sound through the body of water 18 (FIG. 2). The power switch 142 may be a silicon controlled rectifier circuit, thyratron circuit or relay circuit which is normally closed to permit electrical signals to pass through it but capable of being opened by the application of a signal to a control input 148 and resetable by the application of a signal to a reset input terminal 154. Such circuits are well-known in the art.

To cause the power switch 142 to open, a threshold detector 140 has its input electrically connected to cable 32 and its output electrically connected to one of the inputs of a two-input AND gate 144. The other input of the AND gate 144 is electrically connected to conductor 23 and its output is electrically connected to the control input 148 of the power switch 142.

With this arrangement, when the signal on cable 32 is sufficient to cause ultrasonic vibrations at above 5 watts per square centimeter in the body of water 18 (FIG. 2), the threshold detector 140 applies a signal to one of the two inputs of the AND gate 144. If the body of water 18 now rises so that the sensor 17 (FIG. 2) senses the intrusion of a person into the tub, the detector 19 (FIG. 2) applies a signal through conductor 23 to the other input of the AND gate 144, causing the power switch 142 to receive a signal from the AND gate 144 and open. This terminates the signal to the transducers on cable 32A and thus the oscillations.

The control system 15 may be any type of capacitance detector. Such capacitance detectors are well-known in the field. Moreover, any other type of detector may be used to detect the intrusion or the proximity of an object to the body of water 18.

A reset switch 151 is electrically connected in series with a source of potential 152 and the reset input terminal 154 so that the ultrasound transducer assembly 30 may be reset by closing the reset switch 151 when the bathing system is again ready for operation. With this construction, an additional protection is provided against the accidental insertion into the bath of a person when high power is being applied for sterilization purposes.

Before being supplied to an end user, the transducer 39A (FIG. 7) is calibrated for the actual tub. This is done by measuring the power with a transducer located where the bather is expected to be and with a standard calibrated meter. The amplifier 80 (FIG. 5) is adjusted until the readout 41 (FIGS. 2 and 5) corresponds in its reading to the reading on the standard meter while the cable 45 is connected to the transducer 39A.

In operation, the operator fills the tub 16 with the body of water 18, adjusts the comfort controls for temperature and type of treatment and, after the patient is in the tub, energizes the arrangement to provide vibrations. The frequency and power density of the vibrations may be set in accordance with the purpose of the unit. For example, cleaning may be performed at a lower power than antimicrobial treatment. The power may be changed during the bathing process so as, for example, to provide microbicidal activity at a first power density before the patient enters the tub and effective cleaning at a lower power density after the patient enters the tub.

To adjust the comfort level, the temperature of the water is controlled by the temperature control 37 (FIG. 2) as water flows from the faucet 26 (FIG. 2) until water has substantially filled the tub 16 or filled it to the desired level for treatment. The power density is then set by adjusting the dial 33 (FIG. 2), which adjusts the autotransformer 64 (FIG. 4).

To begin the treatment, the mains power switch 53 (FIG. 4) is closed which then applies power to the ground fault interrupter 55 and to the isolation transformer 62 so that the frequency converter 66 begins sweeping at its preset frequency, which normally will be 26.5 kilohertz with a 1 kilohertz sweep frequency. Although the frequency converter in the preferred embodiment is capable of providing up to 500 watts power, much lower powers are provided. The power is selected to result in the desired power density within the fluid by monitoring the fluid as the power is adjusted by the dial 37 (FIG. 2).

The power is monitored by measuring the power of the vibrations on the transducer 39 (FIG. 2) and transmitting signals representing this power to the amplifier 80 (FIG. 5) which amplifies it and transmits it to the analog-to-digital 82 (FIG. 5) converter which converts it to digital form and transmits it to the LED display 41 (FIG. 5).

To control the power, the dial 37 (FIG. 2) is turned generally until the power is in the range of 0.1 to 5.0 watts per square centimeter as read on the meter. The dial 37 moves the tap on the autotransformer 64 (FIG. 4) to control the voltage applied to the frequency converter 66. The power generated by the ultrasonic generator 28 is applied through the cable 32 to the ultrasound transducer assembly 30 (FIGS. 2, and 6-8) which results in vibrations being applied through the nickel plate 30 to the bath where they are applied to the patient and sensed by the transducer 39 (FIG. 2). Generally, the power is applied for fifteen minutes or less and at a power and frequency which will not result in transient cavitation of the blood but yet to perform hygienic, antimicrobial or therapeutic treatment.

If a ground fault is created, the current through the ground connection of the ground fault interrupter 55 (FIG. 4) causes it to open the circuit and terminate operation. Moreover, if the power density in the water 18 exceeds the amount set in the threshold detector 92 (FIG. 6), the relay solenoid 102 opens the circuit containing solenoid coil 57 (FIG. 4) through relay switch 61, causing the normally open mains power switch 53 to open. If this safety circuit fails, three-pole double-throw, relay operated switch 94 energizes warning lamp 96 and flasher 98 to provide an alarm.

In one embodiment, ultrasonic vibrations are applied at a power density of above 30 watts per square centimeter. In this embodiment, an additive is desirable, which may weaken cells walls of microbes or oxidize microbes. The ultrasonic vibrations at high power by themselves may sterilize the water and inanimate objects in it but the combination of additives for cleaning and further antiseptic reasons synergistically sterilze the water and, if desired, may clean and sterilize inanimate objects such as instruments and the like.

A detector in this embodiment detects the presence of a person or other object while the high power is being applied. For example, capacitance detectors may detect any time the water rises in the container. The detection will immediately de-energize or insert an attenuator in circuit with the ultrasonic generator to reduce the power density before damage can be done to a person who may accidentally enter the body of water.

When the water has been sterilized, in some embodiments such as those that are used for bathing or other treatment of animals, the power may be reduced to a level that is not irritating or damaging. The patient or other animal may then enter the bath and be subject to its cleaning action or other beneficial action from the bath without fear of contamination from the water.

From the above description, it can be understood that the apparatus and method of this invention has several advantages over the prior art, such as: (1) it has hygienic, therapeutic and antimicrobial benefits while being harmless to animals; (2) it makes economical use of vibrating transducers by avoiding standing waves and using low attenuation water as a working fluid; and (3) performs both cleaning and healing benefits while at the same time provide antiviral, antibacterial and antifungal activity in a manner making it suitable for treatment of certain particularly severe maladies such as treating patients with severe burns.

Although a preferred embodiment of the invention has been described with some particularity, many modifications and variations in the invention are possible within the light of the above teachings. Therefore, it is to be understood, that within the scope of the appended claims, the invention may be practiced other than as specifically described.

What is claimed is:

1. A method of treating animals in a working fluid contained within wall means comprising the steps of:
   transmitting ultrasonic vibrations at a power density in excess of 15 watts per square centimeter through the working fluid during a first time period in which no portion of the animal is immersed in said working fluid, whereby the working fluid is sterilized;
   immersing a body portion of the animal into the working fluid during a second time period different than the first time period with the body portion being in acoustic contact with the working fluid; and
   applying ultrasonic vibrations through the working fluid to the body portion at a frequency in a range of 15 kilohertz to 100 kilohertz and a power density below 5 watts per square centimeter during the second time period.

2. A method according to claim 1 further including the step of absorbing a portion of said ultrasonic vibrations in said wall means, whereby transmission to air of ultrasonic sound and subharmonics of the ultrasonic sound in an audible range are reduced.

3. A method according to claim 1 in which the step of applying ultrasonic vibrations through the working fluid includes the step of applying ultrasonic vibrations in a frequency range which does not cause irritation to humans when transmitted through the air.

4. A method according to claim 1 in which the step of immersing a body portion of an animal includes the step of immersing a body portion of an animal into at least partly degassed water.

5. A method according to claim 1 in which the step of immersing a body portion of an animal includes the step of immersing a body portion of an animal into water in which an additive capable of aiding in at least one of cleaning and antimicrobial action is included.

6. A method in accordance with claim 1 further including the step of detecting the ultrasound in said working fluid and providing an indication of the power density.

7. A method according to claim 6 further including the step of reducing the power density of the ultrasound transmitted into said working fluid when the power density in the working fluid exceeds a predetermined maximum.

8. A method according to claim 7 further including the step of reducing the transmission of said ultrasonic vibrations through said working fluid upon detecting an insertion of a foreign body in said working fluid.

9. A method according to claim 1 in which the step of applying ultrasonic vibrations includes the step of applying ultrasound to a patient with a power density in the range of 0.1 to 5 watts per square centimeter through the working fluid.

10. A method of treating animals comprising the steps of:
   immersing a body portion of the animal into a working fluid with the body portion being in acoustic contact with the working fluid; and
   applying ultrasonic vibrations through the working fluid to the body portion at a frequency in the range of 15 kilohertz to 100 kilohertz and a power density in the range of 0.1 to 5 watts per square centimeter through the working fluid for a time less than 15 minutes and at a power and frequency that does not cause transient cavitation.

11. A method of treating animals comprising the steps of:
   immersing a body portion of the animal into a working fluid with the body portion being in acoustic contact with the working fluid;
   applying ultrasonic vibrations through the working fluid to the body portion at a predetermined frequency in a frequency range of 15 kilohertz to 100 kilohertz; and
   modulating the predetermined frequency with a sweep frequency across a predetermined sweep frequency band.

12. Apparatus for ultrasonic treatment of animals comprising:
   container means adapted to contain a working fluid in which at least a portion of an animal may be immersed for treatment by ultrasonic vibrations; and
   means for applying ultrasonic vibrations through the working fluid within the container means in two selected frequency ranges differing from each other at least in power denisty during corresponding ones of two different time periods, wherein one of said selected frequency ranges is in a power density range of less than 15 watts per square centimeter and frequency range between 15 kilohertz and 100 kilohertz and the other selected frequency range is in a power density range greater than 15 watts per square centimeter.

13. Apparatus according to claim 12 wherein the power density in the working fluid that is in contact with the animal is between 0.1 and 5 watts per square centimeter.

14. Apparatus according to claim 12 in which at least one of the container means and the means for applying ultrasonic vibrations to the working fluid includes a material which absorbs sound of the frequency used.

15. Apparatus according to claim 12 further including a degasser adapted to remove at least some gas from water and positioned to fill the container means with at least partly degassed water.

16. Apparatus according to claim 12 further including probe means for sensing power intensity of said ultrasonic vibrations in said working fluid.

17. Apparatus according to claim 16 further including means for reducing the power density emitted by said means for applying ultrasonic vibrations when the power density measured by said probe means exceeds a predetermined value.

18. Apparatus according to claim 12 further including:
   means for sensing an intrusion of an object into said working fluid; and
   means for reducing the power density transmitted by said means for applying ultrasonic vibrations upon sensing the intrusion of said object into said working fluid.

19. Apparatus for ultrasonic treatment of animals comprising:
   container means adapted to contain a working fluid in which at least a portion of an animal may be immersed for treatment by ultrasonic vibrations;
   means for applying ultrasonic vibrations in a first frequency range of between 15 kilohertz and 100 kilohertz through the working fluid within the container means; and
   means for modulating the first frequency of the ultrasonic vibrations with a second sweep frequency across a second frequency band centered on the first frequency.

20. Apparatus in accordance with claim 19 in which the range of the power density within the working fluid and in contact with the portion of the animal is less than 15 watts per square centimeter.

21. Apparatus according to claim 20 in which the power density of the ultrasound in the working fluid that is in contact with the animal is between 0.1 and 5 watts per square centimeter.

22. Apparatus for ultrasonic treatment of animals comprising:
   container means adapted to contain a working fluid in which at least a portion of an animal may be immersed for treatment by ultrasonic vibrations; and
   means for applying ultrasonic vibrations in a frequency range of between 15 kilohertz and 100 kilohertz through the working fluid within the container means;
   said means for applying ultrasonic vibrations including a vibrator and an interface;
   said interface including a glass plate mounted to said container means and positioned to be vibrated by said vibrator wherein said vibrations are transmitted to said working fluid.

* * * * *